(12) United States Patent
Noguchi (10) Patent No.: US 8,680,494 B2
(45) Date of Patent: Mar. 25, 2014

(54) POLYMERIZATION APPARATUS FOR DENTAL TECHNOLOGY

(75) Inventor: Yukie Noguchi, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 13/541,136

(22) Filed: Jul. 3, 2012

(65) Prior Publication Data

US 2013/0017124 A1   Jan. 17, 2013

(30) Foreign Application Priority Data

Jul. 11, 2011   (JP) .................. 2011-152718

(51) Int. Cl.
*G21K 5/04* (2006.01)
(52) U.S. Cl.
USPC ................ 250/504 R; 250/492.1; 250/494.1; 433/2; 433/6; 433/215; 433/226
(58) Field of Classification Search
USPC ........ 250/2, 6, 215, 229, 492.1, 493.1, 494.1, 250/504 R
See application file for complete search history.

(56) References Cited

U.S. PATENT DOCUMENTS

| | | | |
|---|---|---|---|
| 2003/0215766 A1* | 11/2003 | Fischer et al. | 433/29 |
| 2005/0205882 A1* | 9/2005 | Condon | 257/88 |
| 2007/0187612 A1* | 8/2007 | Inoue et al. | 250/372 |
| 2010/0196827 A1* | 8/2010 | Leenders et al. | 430/306 |

FOREIGN PATENT DOCUMENTS

| | | |
|---|---|---|
| CA | 2190226 A1 | 6/1997 |
| DE | 86 27 655.7 U1 | 4/1987 |
| EP | 0128324 A1 | 12/1984 |
| EP | 0780104 A2 | 6/1997 |
| JP | 2003-033374 A | 2/2003 |
| JP | 4130372 B2 | 8/2008 |
| JP | 4403315 B2 | 1/2010 |

OTHER PUBLICATIONS

European Search Report date Oct. 15, 2012; Appln. No. 12174874.3-1269.

* cited by examiner

*Primary Examiner* — Nicole Ippolito (74) *Attorney, Agent, or Firm* — Ladas & Parry LLP (57) ABSTRACT

Polymerization apparatus for dental technology, having a housing; a partition wall disposed in the housing so as to form a polymerization space where polymerization is carried out; a rotating table, which is arranged on a lower side of the polymerization space and on which the dental prosthesis is disposed directly or via other members; and a plurality of LED light sources which irradiate a light for the curing to a polymerization region, which is formed on the upper side of the rotating table and where the dental prosthesis can be disposed, wherein at least one of the plurality of LED light sources is disposed such that a light axis thereof is inclined obliquely upward to be directed toward the polymerization region.

10 Claims, 5 Drawing Sheets

POLYMERIZATION APPARATUS FOR DENTAL TECHNOLOGY

TECHNICAL FIELD

The present invention relates to a polymerization apparatus for dental technology which is used in making a dental prosthesis and the like in the field of dentistry, particularly in the field of dental technology, and which cures a light curing material.

BACKGROUND ART

In the field of dentistry, particularly in the field of dental technology, when making a dental prosthesis such as a dental restorative material and a denture base, a method is widely employed of forming a shape of the dental prosthesis with a before-curing light curing material and fixing the shape by irradiating light to harden the light curing material. Herein, an apparatus which irradiates light to cure (polymerize) the light curing material is the polymerization apparatus for dental technology.

Conventionally, a fluorescent lamp, halogen lamp, xenon lamp, and the like have been used as a light source of a polymerization apparatus for dental technology. However, these light sources do not necessarily have long life; thus it is necessary to change the light sources quite frequently. Further, many of the commercially available light curing materials for dental purposes can be cured (polymerized) with a blue or purple light having a short wavelength. However, the above described light sources emit a light with a wide wavelength range, thus including a wavelength outside the wavelength range necessary to cure the light curing material. As such, these light sources use energy in excess in the unnecessary wavelength range; thus effective irradiation of light cannot be expected.

On the other hand, Patent Documents 1, 2 disclose a polymerization apparatus for dental technology using a light-emitting diode (LED), wherein a plurality of light-emitting diodes which emit a light with a specific wavelength range, thereby enabling more effective irradiation of light than before.

CITATION LIST

Patent Documents

Patent Document 1: Japanese Patent No. 4403315
Patent Document 2: Japanese Patent No. 4130372

SUMMARY OF THE INVENTION

Problems to be Solved by the Invention

However, a dental prosthesis to be polymerized has a very complex surface shape because it is modeled after a tooth or a tooth row; thus it has been demanded that polymerization can be carried out effectively and evenly for such a complex shape. In order to be able to carry out polymerization evenly, for example a plurality of light-emitting diodes may be disposed, as described in Patent Document 1 (see [0025]). However, in view of replacement of light sources and power consumption, the number of light sources to be used is preferably as small as possible.

Accordingly, in view of the above problems, an objective of the present invention is to provide a polymerization apparatus for dental technology which is capable of carrying out effective polymerization with a reduced number of LED light sources to be used.

Means for Solving the Problems

The present invention will be described hereinafter. It should be noted that although the reference numerals given in the drawings are also shown herein for the purpose of easy understanding, the present invention is not limited thereto.

A first aspect of the present invention is a polymerization apparatus (10, 20) for dental technology which cures a light curing material to be used for a dental prosthesis (1), the polymerization apparatus for dental technology comprising: a housing (11); a partition wall (13, 23) disposed in the housing so as to form a polymerization space (A) where polymerization is carried out; a rotating table (14) which is arranged on a lower side of the polymerization space and on which the dental prosthesis is disposed directly or via other members; and a plurality of LED light sources (15b, 15c) which irradiate a light for the curing to a polymerization region (B), which is formed on the upper side of the rotating table and where the dental prosthesis can be disposed, wherein at least one (15c) of the plurality of LED light sources is disposed such that a light axis thereof is inclined obliquely upward to be directed toward the polymerization region.

Here, the "light axis" refers to a direction in which brightness is the highest in a brightness distribution of the light emitted from one LED light source. The same shall apply hereinafter.

A second aspect of the present invention is the polymerization apparatus (10, 20) for dental technology according to the first aspect, which is provided with a plurality of LED light sources (15c) disposed such that a light axis thereof is inclined obliquely upward to be directed toward the polymerization region (B), wherein at least one of the plurality of LED light sources is a purple or near-ultraviolet LED.

Herein, the LED light source emitting a purple light means that it has a peak wavelength within a range of 380 nm or more and less than 440 nm; and the LED emitting a near-ultraviolet light means that it has a peak wavelength within a range of 315 nm or more and less than 380 nm.

Particularly preferred is a light having a peak wavelength within a range of 370 nm to 410 nm enabled by the LED emitting near-ultraviolet light or the LED emitting a purple light.

A third aspect of the present invention is the polymerization apparatus (10, 20) for dental technology according to the first aspect, wherein a height adjustment member is disposed on the rotating table or the rotating table itself is configured to be movable up and down in order to adjust the height position of the dental prosthesis (1) in the polymerization region (B).

A fourth aspect of the present invention is the polymerization apparatus (10, 20) for dental technology according to the first aspect, wherein at least one (15b) of the plurality of LED light sources is disposed such that a light axis thereof is inclined obliquely downward to be directed toward the polymerization region (B).

Effects of the Invention

According to the polymerization apparatus for dental technology of the present invention, it is possible to carry out polymerization effectively with a reduced number of LED light sources to be used.

MODES FOR CARRYING OUT THE INVENTION

The functions and benefits of the present invention described above will be apparent from the following modes for carrying out the invention. However, the invention is not limited to the embodiments.

Figure 1:
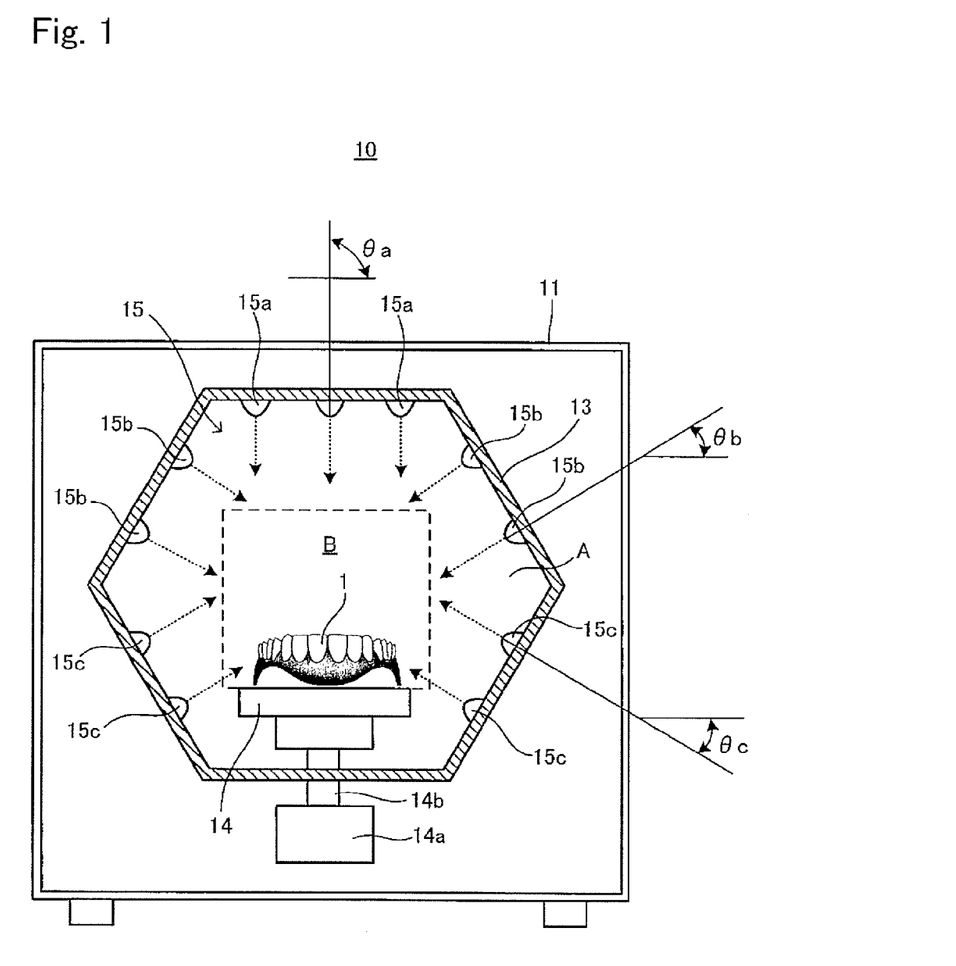
FIG. 1 is a front view conceptually showing a configuration of a polymerization apparatus for dental technology according to one embodiment.
Figure 2:
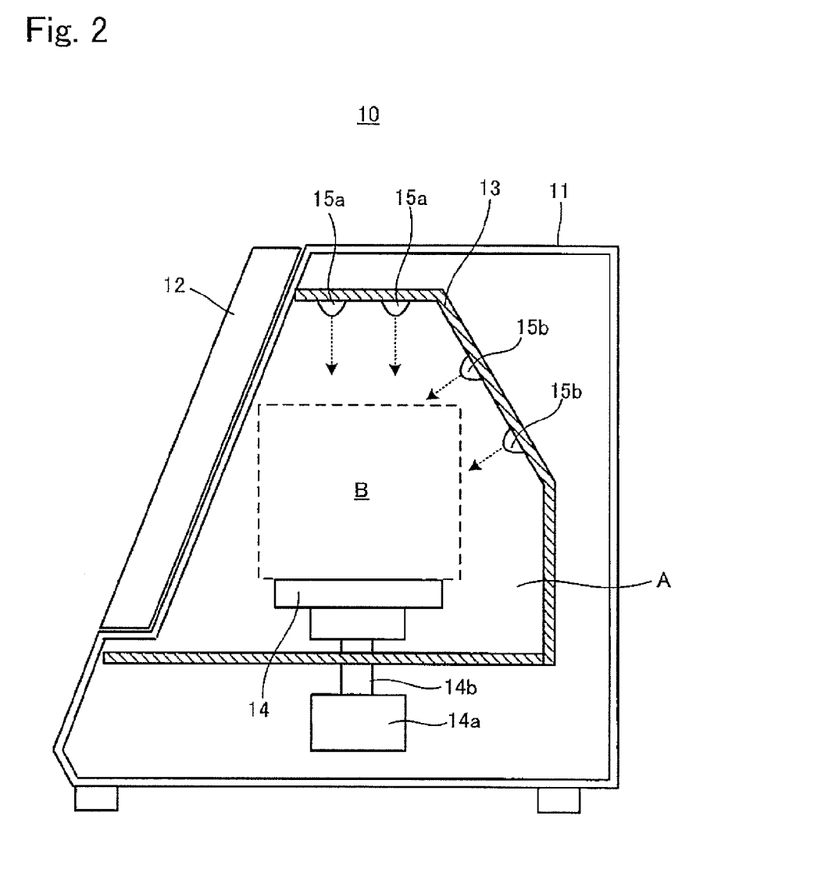
FIG. 2 is a side view conceptually showing a configuration of a polymerization apparatus for dental technology according to one embodiment.

FIGS. 1 and 2 are views conceptually showing the configuration of the polymerization apparatus 10 for dental technology according to one embodiment. FIG. 1 is front view and FIG. 2 is a side view.

The polymerization apparatus 10 for dental technology comprises a housing 11; a lid 12; a partition wall 13; a rotating table 14; and a group 15 of LED light sources. Each of the configurations thereof will be described hereinafter. In addition to these components, the polymerization apparatus 10 for dental technology is also provided with known devices (e.g. power-supply device, electrical circuit, electrical wiring) for the polymerization apparatus 10 for dental technology to function. Furthermore, the polymerization apparatus 10 for dental technology may be provided with a device for releasing the heat generated from the group 15 of LED light sources.

As can be seen from FIGS. 1 and 2, the housing 11 is a member to form an outer shell of the polymerization apparatus 10 for dental technology; and most of the members to compose the polymerization apparatus 10 for dental technology are disposed inside the housing 11.

The lid 12 serves as part of a wall forming the polymerization space A in combination with the below described partition wall 13; and is a lid member disposed in a manner covering an opening provided to the housing 11. The lid 12 is openable and closable: at the time of opening, the polymerization space A can be communicated with the outside; and at the time of closing, the polymerization space A is closed. In specific, it is possible to open the lid 12 to put a dental prosthesis 1 and the like in the polymerization space A and to take it out of the polymerization space A; and the dental prosthesis 1 is irradiated with light, with the lid 12 closed.

The partition wall 13 is a member to form the polymerization space A in the housing 11, in which space polymerization is carried out. As shown in FIGS. 1 and 2, a plurality of board-like members are combined three-dimensionally. As can be seen from FIG. 1, in the present embodiment, the plurality of board-like members are combined to form a hexagonal shape when seen from the front. In this manner, it is preferable that the polymerization space be formed by the partition wall in a polygonal shape when seen from the front (viewpoint in FIG. 1) or from the side (viewpoint in FIG. 2); and that the light be emitted from at least two faces thereof by the LEDs 15b, 15c having a light axis in the normal direction of the face. By this, the light can be surely irradiated to the upper face (occlusal face) of the dental prosthesis 1 by the LED 15b; to the side face having a large surface area by the LEDs 15b, 15c; and to the undercut portion by the LED 15c. Accordingly, it is possible to irradiate the light so as to match the shape of the dental prosthesis 1 with a small number of LEDs. The undercut portion will be explained later. In specific, as described below, the dental prosthesis 1 is irradiated with the light having a light axis being horizontal or obliquely inclined such as LED 15b, LED 15c; thereby it is possible to irradiate light to a large area in combination with rotation of the dental prosthesis 1 by the rotating table 14.

It should be noted that the configuration of the partition wall is not particularly restricted as long as it can form the polymerization space A; for example it may be in a dome shape having a curved surface, or a part of a hollow spherical shape.

The rotating table 14 is a table-like member which is arranged in the bottom area of the polymerization space A formed by the partition wall 13, and which can be rotated by a motor 14a. The dental prosthesis 1 is disposed on the rotating table 14 directly, or via for example a block-like or board-like height adjustment member (not shown) having a predetermined thickness for adjusting the height position. The rotating table 14 is attached to the axis 14b rotated by the motor 14a, thereby enabling the rotating table 14 itself to rotate. Accordingly, the dental prosthesis 1 disposed thereon can also be rotated, enabling further uniform curing (polymerizing).

As is apparent from the configuration that the dental prosthesis 1 is disposed on the rotating table 14 in this manner, the polymerization region B is formed on the upper side of the rotating table 14. The polymerization region B is a region in the polymerization space A, in which region the dental prosthesis 1 can be actually disposed to carry out polymerization.

In order to adjust the height position of the dental prosthesis 1 in the polymerization region B, the height adjustment member may be employed as described above; the rotating table 14 itself may be configured to be movable up and down. The mechanism for allowing the rotating table 14 to be movable up and down is not particularly restricted; however, example may include a configuration that the axis 14b which rotates the rotating table 14 is made movable up and down.

The group 15 of LED light sources are formed of a plurality of light-emitting diodes (LED) 15a, 15b, 15c; and each of the LEDs 15a, 15b, 15c are disposed on the face of the partition wall 13, the face being on the side of the polymerization space A. The light axes of the LED 15a, LED 15b, and LED 15c are directed toward the polymerization region B; however, the directions of the light axes are different among the LED 15a, LED 15b, and LED 15. Here, the "light axis" refers to the direction in which brightness is the highest in the brightness distribution of the light emitted from the LED. Details are as follows.

The LED 15a is an LED light source which is arranged on the upper partition wall 13 to emit light toward the polymerization region B positioned ranging from the upper side of the polymerization space A to the lower side. In specific, in a posture that the dental prosthesis is cured (polymerized) by the polymerization apparatus 10 for dental technology, when an angle that the light axis of the LED 15a makes with the horizontal face is defined as θa, θa is 90°.

The LED 15b is an LED light source which is arranged on the lower partition wall 13 than the LED 15a to emit light from the side area of the polymerization space A toward the polymerization region B horizontally or obliquely downward. In specific, in a posture that the dental prosthesis 1 is cured (polymerized) by the polymerization apparatus 10 for dental technology, when the light axis of the LED 15b is directed toward the polymerization region B and the angle that the light axis thereof makes with the horizontal face is defined as θb, it is 0≤θb<90°. In cases where the LED 15a is not provided, it is more preferably 30°≤θb<90°.

The LED 15c is an LED light source which is arranged on the lower partition wall 13 than the LED 15b to emit light from the side area of the polymerization space A toward the polymerization region B obliquely upward. In specific, in a posture that the dental prosthesis 1 is cured (polymerized) by the polymerization apparatus 10 for dental technology, when the light axis of the LED 15c is directed toward the polymerization region B and the angle that the light axis thereof makes with the horizontal face is defined as θc, it is θc<0°.

Here, the positive and negative of the angle is as follows: when the light axis is directed downward, the angle is positive; when the light axis is directed upward, the angle is negative.

The LEDs 15a, 15b, 15c are light-emitting diodes (LED) which emit the light including a wavelength necessary for curing a light curing material to be used for the dental prosthesis 1. Usually, this wavelength range in which the light curing material is cured is 360 nm to 500 nm; thus a near-ultraviolet, purple, blue, or white LED is preferable. Typical examples of the light curing material include a resin material using camphorquinone for the photopolymerization catalyst. A wavelength in which the light curing material starts to be cured (polymerized) is approximately 470 nm.

Herein, the LED which emits a near-ultraviolet light refers to a light having a peak wavelength within a range of 315 nm or more and less that 380 nm. Likewise, the LED which emits a purple light refers to a light having a peak wavelength within a range of 380 nm or more and less that 440 nm; and the LED which emits a blue light refers to a light having a peak wavelength within a range of 440 nm or more and less that 550 nm. The LED which emits a near-ultraviolet light is preferably a light having a peak wavelength within a range of 370 nm or more and less than 380 nm. Likewise, the LED which emits a purple light is preferably a light having a peak wavelength within a range of 380 nm to 410 nm; and the LED which emits a blue light is preferably a light having a peak wavelength within a range of 450 nm to 490 nm.

The arrangements of the near-ultraviolet, purple, blue, and white LEDs are not particularly restricted: one kind of these may be provided; two or three kinds of LEDs may be provided. Furthermore, a multi-chip type LED wherein a plurality of LED elements are mounted in one package may be employed.

The number of LEDs to be disposed is not particularly restricted; however, it is preferable to dispose the LED 15b, LED 15c and to provide a plurality of LEDs to each of them. Further, in view of a curing property of the commercially available light curing materials, at least one of the plurality of LEDs 15b is further preferably a near-ultraviolet, purple, or blue LED. Likewise, at least one of the plurality of LEDs 15c is preferably a near-ultraviolet, purple, or blue LED. Especially, with regard to the LED 15c, in order to effectively polymerize the undercut portions C, D (see FIG. 3) of the dental prosthesis 1 as described below, at least one of the LEDs 15c preferably includes a near-ultraviolet or purple LED.

In the present embodiment, the LED 15a is formed of three blue LEDs; the LED 15b is formed of eight blue LEDs and one purple LED; and the LED 15c is formed of five blue LEDs and one purple LED.

With the polymerization apparatus 10 for dental technology 10 comprising the above described components, it is possible to form the dental prosthesis 1 for example in the following manner.

The dental prosthesis 1 shaped by a before-curing light curing material is disposed inside the polymerization region B positioned on the rotating table 14 in the housing 11. At this time, the dental prosthesis 1 may be put directly on the rotating table 14, or it may be arranged on the rotating table 14 via a height adjustment member for adjusting the height position of the dental prosthesis 1. Further, if the rotating table 14 itself is configured to be movable up and down, this can be used to adjust the height position of the dental prosthesis.

Next, the lid 12 is closed to turn on the LED 15a, LED 15b, LED 15c and to rotate the rotating table 14. Thereby the light curing material of the dental prosthesis 1 starts to be cured (polymerized) by the light emitted from the LED 15a, LED 15b, and LED 15c. By continuing irradiation of the light for a certain period of time, the light curing material becomes polymerized and the shape of the dental prosthesis is fixed.

Figure 3:
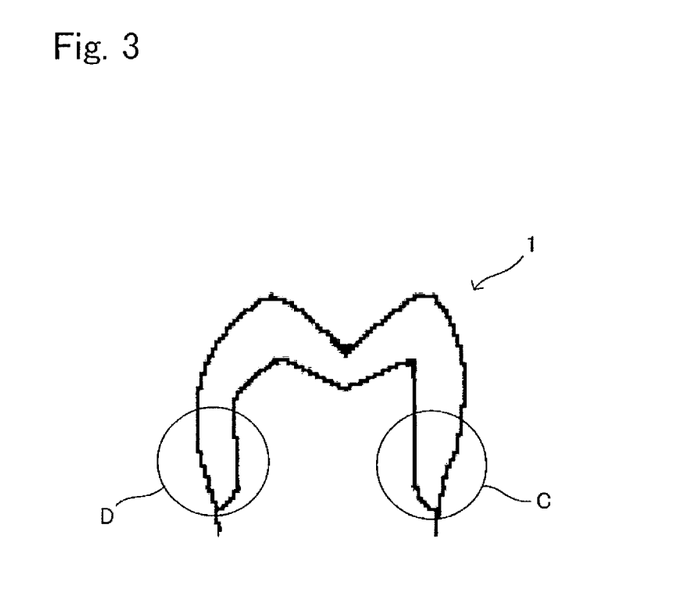
FIG. 3 is a view for illustrating an undercut portion of a dental prosthesis.

Herein, the polymerization apparatus 10 for dental technology is provided with LED light sources, such as LED 15a and LED 15b, which irradiate light from the upper area or side area toward the polymerization region B; in addition, it is also provided with the LED 15c which irradiates light obliquely from the lower area toward the polymerization region B. Because of this, it is possible to prevent the dental prosthesis 1 having a complex shape from being cured (polymerized) unevenly. More details are as follows. FIG. 3 is an enlarged view of a part of the dental prosthesis 1. The dental prosthesis 1 to be cured (polymerized) is formed by modeling after a human tooth and tooth row; therefore, the surface shape is complicated, and there exist the undercut portions as shown by C and D in FIG. 3. When considering curing (polymerizing) the light curing material in the undercut portions C, D, the light from the upper side cannot reach the undercut portions, and the horizontally-emitted light is insufficient in terms of the light amount, thus inhibiting the undercut portions from being cured (polymerized) or causing the undercut portions to be cured (polymerized) more slowly than the other parts. In the conventional polymerization apparatus for dental technology, it is often necessary to change the positional directions of the dental prosthesis to cure (polymerize) the dental prosthesis again in order to cure (polymerize) the undercut portions. On the other hand, in the polymerization apparatus 10 of dental technology, the LED 15c enables irradiation of light toward the dental prosthesis 1 from the lower side as well; therefore, the undercut portions C, D can be cured (polymerized) as well as the other portions.

With the effective arrangement of the LEDs 15a, 15b, 15c in the polymerization apparatus 10 for dental technology as described above, it is possible to reduce the number of LEDs to be used. For example, in the present embodiment, three LEDs 15a, nine LEDs 15b, and six LEDs 15c are provided as described above; thus a total of 18 LEDs are provided. The number of LEDs to be provided is not limited to this; a minimum of one LED 15b and one LED 15c may be provided. However, in order to shorten the polymerization time by disposing a plurality of each of the LEDs 15b and LEDs 15c, it is preferable to arrange a minimum of 2 LEDs 15b (e.g. one blue LED and one purple LED), a minimum of 2 LEDs 15c (e.g. one blue LED and one purple LED).

Further, in this case the LED 15a shown in FIG. 1 is not arranged as described above; therefore the angle θb shown in FIG. 1 is preferably 30°≤θb<90°.

Furthermore, if a table on which to dispose the dental prosthesis 1 is configured to be rotatable like the rotating table 14, it becomes possible to irradiate light more effectively by rotating the table.

Figure 4:
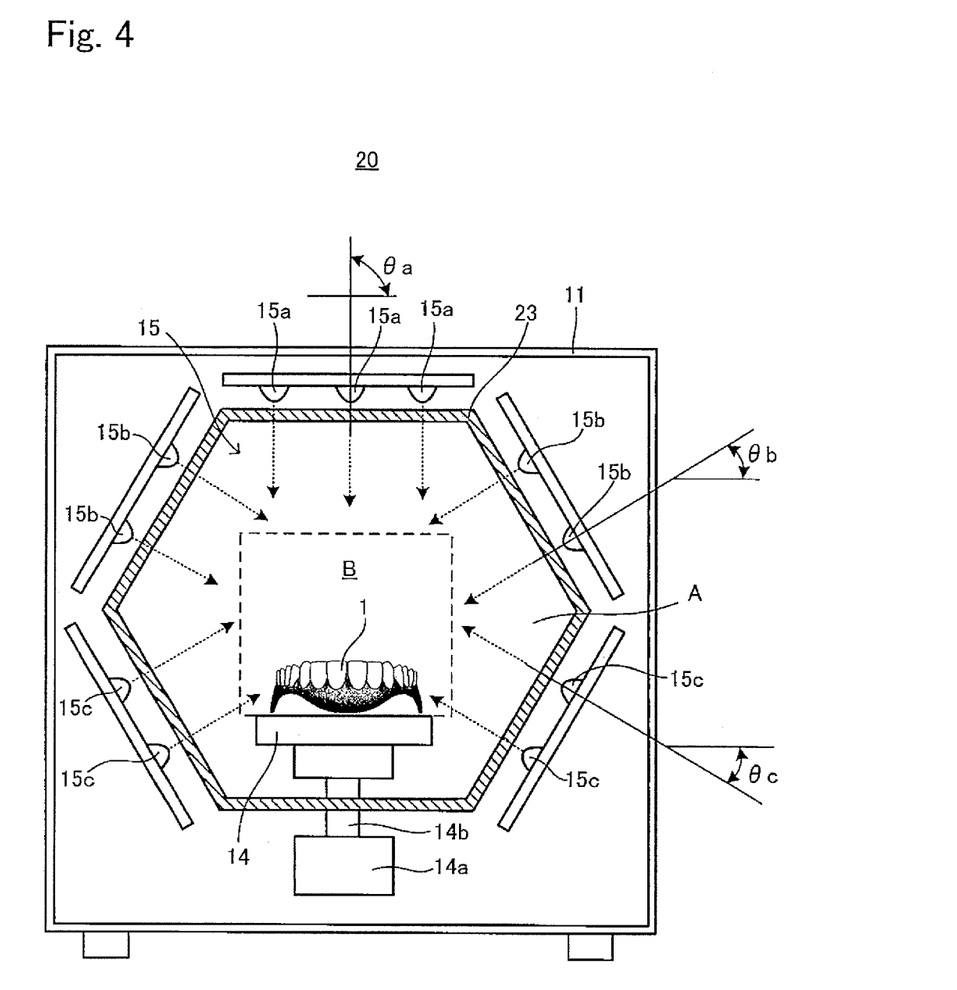
FIG. 4 is a front view conceptually showing a configuration of a polymerization apparatus for dental technology according to another embodiment.
Figure 5:
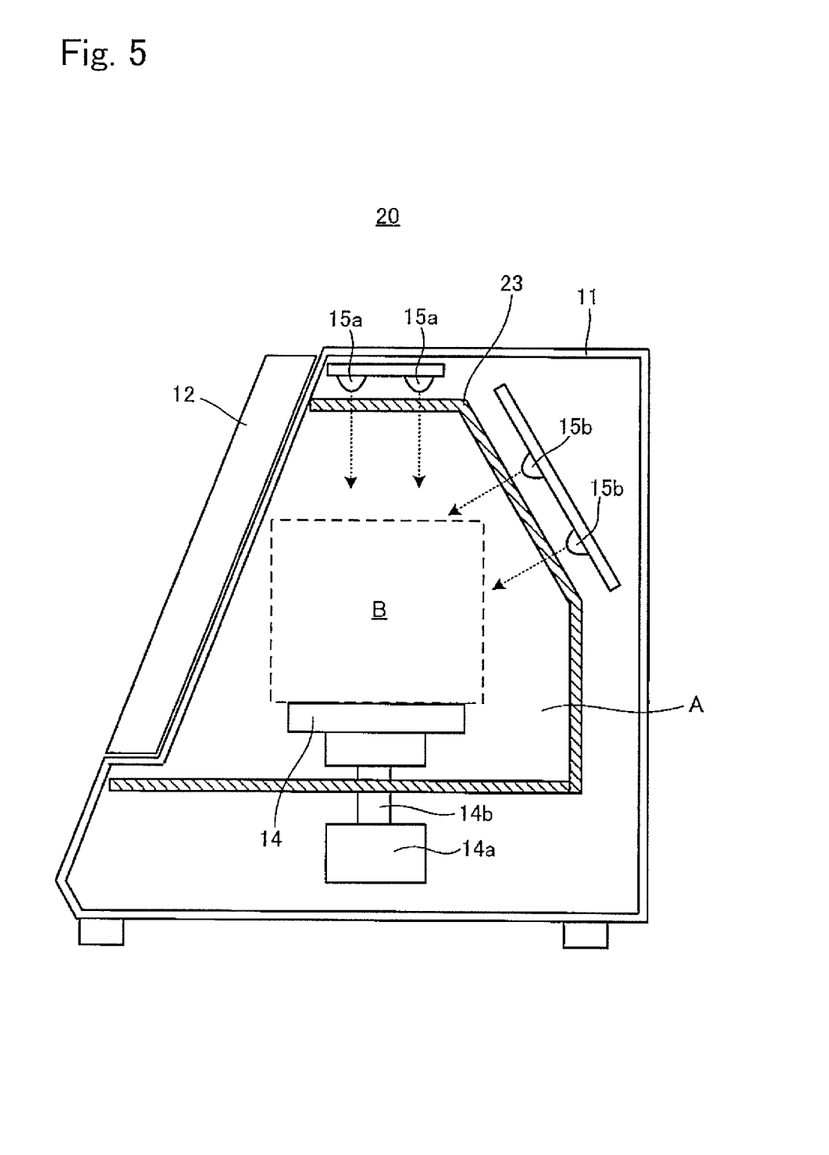
FIG. 5 is a side view conceptually showing a configuration of a polymerization apparatus for dental technology according to another embodiment.

Next, the polymerization apparatus 20 for dental technology in another embodiment will be described. FIGS. 4 and 5 conceptually illustrate the configuration of the polymerization apparatus 20 for dental technology in another embodiment. FIG. 4 is a view of the polymerization apparatus 20 for dental technology seen from the front; and FIG. 5 is a view seen from the side face.

The polymerization apparatus 20 for dental technology comprises a housing 11; a lid 12; a partition wall 23; a rotating table 14; and a group 15 of LED light sources. In addition to these, the polymerization apparatus 20 for dental technology is also provided with known devices (e.g. power-supply device, electrical circuit, electrical wiring) for the polymerization apparatus 20 for dental technology to function. Furthermore, the polymerization apparatus 20 for dental technology may be provided with a device for releasing the heat generated from the group 15 of LED light sources.

The configuration of the polymerization apparatus 20 for dental technology is the same in some parts as the above described configuration of the polymerization apparatus 10 for dental technology. Thus, the same parts will be given the same numerals; and the descriptions thereof will be omitted.

The polymerization apparatus 20 for dental technology of the present embodiment differ from the polymerization apparatus 10 for dental technology in that: at least the area, of the partition wall 23, around the part that the LED light axis intersects is formed of a light-transmissive material; and the group 15 of LED light sources are provided on the outer side thereof. The light-transmissive material is not particularly restricted; however, for the purpose of diffusing or converging the light from the group 15 of LED light sources, a lens may be provided herein. Further, the light-transmissive material may comprise two or more layers having different materials on the polymerization space A side and the outer side. For example, a transparent resin film or a thin sheet may be provided on the polymerization space A side; and a resin lens or a glass lens may be provided on the more outer side. By this, even if the side of the light-transmissive material which is exposed to the polymerization space A side becomes dirty because of the material to be cured (polymerized), only the layer on the polymerization space A side may be replaced, thus enabling prevention of the attenuation of light amount caused by the stains and damages of the light-transmissive material.

Specifically, in the polymerization apparatus 20 for dental technology, the polymerization space A is formed by the partition wall 23 which transmits light, and the light is irradiated from the outer side thereof. With this configuration, the polymerization apparatus 20 for dental technology can exert similar effects as that of the polymerization apparatus 10 for dental technology and can protect the LEDs 15*a*, 15*b*, 15*c* from the stains and the like. Further, by separating the polymerization space A from the LEDs 15*a*, 15*b*, 15*c*, it is possible to effectively release the heat generated from the LEDs 15*a*, 15*b*, 15*c* to the outside without causing an influence to the inside of the polymerization space A.

DESCRIPTION OF THE REFERENCE NUMERALS

10, 20 polymerization apparatus for dental technology
11 housing
12 lid
13, 23 partition wall
14 rotating table
15 group of LED light sources

The invention claimed is:

1. A polymerization apparatus for dental technology which cures a light curing material to be used for a dental prosthesis, the polymerization apparatus for dental technology comprising:
   a housing;
   a partition wall disposed in the housing so as to form a polymerization space where polymerization is carried out;
   a rotating table, which is arranged on a lower side of the polymerization space and on which the dental prosthesis is disposed directly or via other members; and
   a plurality of LED light sources which irradiate a light for the curing to a polymerization region, which is formed on the upper side of the rotating table and where the dental prosthesis can be disposed,
   wherein at least one of the plurality of LED light sources is disposed such that a light axis thereof is inclined obliquely upward to be directed toward the polymerization region.

2. The polymerization apparatus for dental technology according to claim 1, which is provided with a plurality of LED light sources disposed such that a light axis thereof is inclined obliquely upward to be directed toward the polymerization region, wherein at least one of the plurality of LED light sources is a purple or near-ultraviolet LED.

3. The polymerization apparatus for dental technology according to claim 1, wherein a height adjustment member is disposed on the rotating table or the rotating table itself is configured to be movable up and down in order to adjust the height position of the dental prosthesis in the polymerization region.

4. The polymerization apparatus for dental technology according to claim 1, wherein at least one of the plurality of LED light sources is disposed such that a light axis thereof is inclined obliquely downward to be directed toward the polymerization region.

5. A polymerization apparatus for dental technology which cures a light curing material to be used for a dental prosthesis, the polymerization apparatus for dental technology comprising:
   a housing;
   a partition wall disposed in the housing so as to form a polymerization space where polymerization is carried out, the partition wall having a part formed of a light-transmissive material;
   a rotating table, which is arranged on a lower side of the polymerization space and on which the dental prosthesis is disposed directly or via other members; and
   a plurality of LED light sources which irradiate a light for the curing to a polymerization region, which is formed on the upper side of the rotating table and where the dental prosthesis can be disposed, the plurality of LED light sources being disposed on opposite side of the partition wall from the polymerization region,
   wherein at least one of the plurality of LED light sources is disposed such that a light axis thereof is inclined obliquely upward to be directed toward the polymerization region.

6. The polymerization apparatus for dental technology according to claim 5, which is provided with a plurality of LED light sources disposed such that a light axis thereof is inclined obliquely upward to be directed toward the polymerization region, wherein at least one of the plurality of LED light sources is a purple or near-ultraviolet LED.

7. The polymerization apparatus for dental technology according to claim 5, wherein a height adjustment member is disposed on the rotating table or the rotating table itself is configured to be movable up and down in order to adjust the height position of the dental prosthesis in the polymerization region.

8. The polymerization apparatus for dental technology according to claim 5, wherein at least one of the plurality of LED light sources is disposed such that a light axis thereof is inclined obliquely downward to be directed toward the polymerization region.

9. The polymerization apparatus for dental technology according to claim 5, wherein the part formed of a light-transmissive material of the partition wall comprises a lens to at least either diffuse or collect light from the LED light sources.

10. The polymerization apparatus for dental technology according to claim 5, wherein the partition wall is formed of two or more layers having different materials on a side of the polymerization region and the opposite side of the partition wall from the polymerization region.

\* \* \* \* \*